(12) United States Patent
Attinger

(10) Patent No.: US 10,010,409 B2
(45) Date of Patent: Jul. 3, 2018

(54) INTRAOCULAR LENS INJECTOR, METHOD FOR FOLDING AN INTRAOCULAR LENS AND INTRAOCULAR LENS INJECTOR SYSTEM

(71) Applicant: ATTINGER TECHNIK AG, Stein am Rhein (CH)

(72) Inventor: Jürg Attinger, Stein am Rhein (CH)

(73) Assignee: ATTINGER TECHNIK AG, Stein am Rhein (CH)

( * ) Notice: Subject to any disclaimer, the term of this patent is extended or adjusted under 35 U.S.C. 154(b) by 114 days.

(21) Appl. No.: 15/034,477

(22) PCT Filed: Jun. 17, 2014

(86) PCT No.: PCT/EP2014/062780
§ 371 (c)(1),
(2) Date: May 4, 2016

(87) PCT Pub. No.: WO2015/070994
PCT Pub. Date: May 21, 2015

(65) Prior Publication Data
US 2016/0270907 A1 Sep. 22, 2016

(30) Foreign Application Priority Data
Nov. 15, 2013 (EP) .................... 13193029

(51) Int. Cl.
*A61F 2/16* (2006.01)
*A61F 2/14* (2006.01)
*A61F 9/00* (2006.01)

(52) U.S. Cl.
CPC .............. *A61F 2/167* (2013.01); *A61F 2/148* (2013.01); *A61F 2/1672* (2013.01); *A61F 2/1678* (2013.01); *A61F 9/0017* (2013.01)

(58) Field of Classification Search
CPC ...... A61F 2/167; A61F 2/1678; A61F 9/0017; A61F 2/1672; A61F 2/148
See application file for complete search history.

(56) References Cited

U.S. PATENT DOCUMENTS 7,131,976 B2 * 11/2006 Kobayashi ............ A61F 2/1664
606/107
7,156,854 B2 * 1/2007 Brown ................... A61F 2/1678
606/107

(Continued)

FOREIGN PATENT DOCUMENTS

| EP | 2072025 A1 | 6/2009 |
|---|---|---|
| EP | 2386272 A1 | 11/2011 |
| WO | WO-2004092780 A2 | 10/2004 |

OTHER PUBLICATIONS

International Search Report regarding Application No. PCT/EP2014/062780, dated Sep. 24, 2014.

*Primary Examiner* — Son Dang
(74) *Attorney, Agent, or Firm* — Pearl Cohen Zedek Latzer Baratz LLP

(57) ABSTRACT

IOL (intraocular lens) injector (1) for introducing an IOL (100) into the eye, comprising: an injector body (2); a cavity (4) for holding the IOL (100) comprising a leading haptic (100b) and a trailing haptic (100c); a cartridge (5) ending at a distal end (5c) in an injection nozzle (5a); the injector body (2), the cavity (4) and the cartridge (5) having a channel (6) extending in axial direction (P); and an axially movable pushing plunger (7) being placed in the channel (6) of the injector body (2) for pushing the IOL (100) in axial direction (P) out of the cavity (4) and into the cartridge (5) and the injection nozzle (5a), wherein a folding plunger (8) is arranged in the channel (6) and is extending in axial direction (P), parallel to the pushing plunger (7); and wherein the cavity (4) comprises a trailing haptic rest (4c) for defining (Continued)

the direction of the trailing haptic (100c) of an IOL (100) arrange in the cavity (4), such that the folding plunger (8) when moved in axial direction (P) hits the trailing haptic (100c) of the IOL (100).

12 Claims, 10 Drawing Sheets

(56) References Cited

U.S. PATENT DOCUMENTS

| | | | | | |
|---|---|---|---|---|---|
| 8,460,311 | B2* | 6/2013 | Ishii | | A61F 2/1678 606/107 |
| 8,523,877 | B2* | 9/2013 | Ichinohe | | A61F 2/1662 606/107 |
| 8,523,941 | B2* | 9/2013 | Ichinohe | | A61F 9/0017 606/107 |
| 9,907,647 | B2* | 3/2018 | Inoue | | A61F 2/167 |
| 2001/0007942 | A1* | 7/2001 | Kikuchi | | A61F 2/1672 606/107 |
| 2004/0059343 | A1* | 3/2004 | Shearer | | A61F 2/1664 606/107 |
| 2005/0143750 | A1* | 6/2005 | Vaquero | | A61F 2/1664 606/107 |
| 2006/0235437 | A1* | 10/2006 | Vitali | | A61B 17/10 606/142 |
| 2008/0039862 | A1* | 2/2008 | Tran | | A61F 2/1678 606/107 |
| 2008/0119865 | A1* | 5/2008 | Meunier | | A61F 2/1678 606/107 |
| 2008/0200920 | A1* | 8/2008 | Downer | | A61F 2/167 606/107 |
| 2009/0318933 | A1* | 12/2009 | Anderson | | A61F 2/1664 606/107 |
| 2010/0161049 | A1* | 6/2010 | Inoue | | A61F 2/167 623/6.12 |
| 2010/0185206 | A1* | 7/2010 | Ichinohe | | A61F 2/1672 606/107 |
| 2010/0217273 | A1* | 8/2010 | Someya | | A61F 2/167 606/107 |
| 2011/0288557 | A1* | 11/2011 | Kudo | | A61F 2/167 606/107 |
| 2013/0226193 | A1* | 8/2013 | Kudo | | A61F 2/148 606/107 |
| 2014/0135782 | A1* | 5/2014 | Valle | | A61F 2/1691 606/107 |
| 2014/0257317 | A1* | 9/2014 | Safabash | | A61F 2/1678 606/107 |
| 2015/0342726 | A1* | 12/2015 | Deacon | | A61F 2/148 623/6.12 |
| 2017/0258582 | A1* | 9/2017 | Kudo | | A61F 2/1672 |

* cited by examiner

E-E

INTRAOCULAR LENS INJECTOR, METHOD FOR FOLDING AN INTRAOCULAR LENS AND INTRAOCULAR LENS INJECTOR SYSTEM

CROSS REFERENCE TO RELATED APPLICATIONS

This application is a U.S. National Phase under 35 U.S.C. 371 of International Application No. PCT/EP2014/062780, filed Jun. 17, 2014, and published in English as WO 2015070994 on May 21, 2015. This application is based on and claims priority to European Patent Application No. 13193029.9, filed Nov. 15, 2013. The entire disclosures of the above applications are incorporated herein by reference.

FIELD OF THE INVENTION

The field of invention relates to an intraocular lens injector. The field of invention further relates to a method for folding an intraocular lens in an intraocular lens injector. The field of invention further relates to an intraocular lens injector system comprising an intraocular lens injector and an intraocular lens holding container.

BACKGROUND OF THE INVENTION

This invention relates to a device for inserting an intraocular lens (IOL) into the human eye. With recent advances in IOL technology, cataract surgery has transitioned from being solely a treatment for visual rehabilitation to also being a refractive procedure with the aim of improving visual function and ultimately the patient's quality of life. IOLs that increase visual function are for example aspheric IOLs to compensate for the spherical aberration of the cornea, or toric IOLs to correct corneal astigmatism, or IOLs to correct distance vision. The performance of new IOL designs is highly dependent on the position of the IOL in the optical system of the eye. Depending on the type of correction, even little decentration and tilt of an IOL in the eye may decrease visual quality.

Foldable IOLs made from silicone, soft acrylics and hydrogels have become increasingly popular because of the ability to fold or roll such soft lenses and insert them through a small incision. Such an IOL usually consists of a small plastic lens with plastic side struts, called haptics, to hold the lens in place within the capsular bag inside the eye. Such an IOL may be for example a one piece IOL, the haptic material is the same as the optical material, or a three piece IOL, with haptics made of harder material such as polymethylmethacrylate (PMMA) filaments.

The most common technique for inserting a foldable IOL is through an injector. Such injectors use a plunger to squeeze an IOL through a cartridge into the eye. The single piece acrylic and silicone plate haptic IOLs are the simplest to use with injectors. These designs have haptics that are sturdy and to a certain extent are resistant to damage from the plunger, as it forcefully pushes the IOL through the cartridge. The three piece IOLs are more difficult to inject as the haptics are difficult to fold and more fragile and susceptible to plunger damage. It is known to use a dedicated holding and folding forceps, to insert the folded IOL into the injector cartridge before squeezing the IOL into the eye. One disadvantage of such common technique therefore is that haptics will most likely be deformed during the implantation procedure, due to mechanical stress on the haptics during folding with the forceps and/or during insertion with the injector. As a consequence the position of the IOL in the optical system of the eye may not be correct. An additional disadvantage is that the folding of the IOL requires a separate step when preparing the injector for injecting the IOL. An additional disadvantage is that the insertion of a multipiece IOL is less predictable than a single-piece IOL in terms of tilt and decentration. In addition common injectors are not reliable and easy to handle. Two completely different injector systems are known for insertion of a soft, foldable lens. One injector system consists of an injector body (a handpiece) and a separate cartridge, whereby the injector body is reusable or disposable and the separate cartridge is disposable. Another injector system consists of a preloaded injector, which means the lens is packed within the preloaded injector. One disadvantage of such completely different injector systems is that the handling is completely different. This is a potential risk for a surgeon, because the preparation of the injector and the handling of the injector during insertion into the eye are different, so that additional training is required. In practice usually only one type of injector system is used to avoid the risk of improper operation. It is therefore difficult to change from one type of injector system to the other, which restricts flexibility, and increases the cost for stocking and handling the injector system.

Document EP2343029A1 discloses an IOL injector capable of inserting one-piece and three-piece IOLs into the eye. Using a forceps the IOL has to be taken out from its packaging and has to be placed very carefully into the injector. In particular the haptics have to be placed very carefully in the correct position. Disadvantages of this injector are that inserting the IOL into the injector is difficult and demanding, that the IOL, in particular the haptics might be damaged during insertion of the IOL into the injector, and that the haptics might be damaged when the plunger folds the haptic and squeezes the IOL through the injection tube.

Document WO2012/015300A1 discloses an IOL injector capable of inserting IOLs into the eye. A high pressure is acting onto the haptics when the plunger folds the haptic and squeezes the IOL through the injection tube, therefore the haptics might be damaged.

Document EP2386272A1 discloses a preloaded IOL injector capable of inserting IOLs into the eye. Disadvantages of this IOL injector are that it is difficult to handle when inserting the IOL into the eye, and that handling errors may occur during insertion. In addition the IOL injector is only suitable for preloaded systems.

Technical Problem to be Solved

The objective of the present invention is thus to provide an IOL injector as well as an IOL injector system that is easy, versatile and reliable to handle.

It is also an objective of the present invention to limit mechanical stress onto the IOL, to in particular avoid deformation of the haptics.

It is also an objective of the present invention to provide an advantageous and reliable method for folding the IOL within the IOL injector.

SUMMARY OF THE INVENTION

The above-identified objectives are solved by an IOL injector comprising the features of claim 1 and more particular by an injector comprising the features of claims 2 to 10. The objectives are further solved by a method for folding an IOL comprising the features of claim 11 and more particular by a method comprising the features of claim 12. The objectives are further solved by an IOL injector system comprising the features of claim 13, and more particular by a system comprising the features of claim 14.

The objective is in particular solved by IOL (intraocular lens) injector for introducing an IOL into the eye, comprising: an injector body; a cavity for holding the IOL comprising a leading haptic and a trailing haptic; a cartridge ending at a distal end in an injection nozzle; the injector body, the cavity and the cartridge having a channel extending in axial direction; and an axially movable pushing plunger being placed in the channel of the injector body for pushing the IOL in axial direction out of the cavity and into the cartridge and the injection nozzle, wherein a folding plunger is arranged in the channel and is extending in axial direction, parallel to the pushing plunger; and wherein the cavity comprises a trailing haptic rest for defining the direction of the trailing haptic of an IOL arrange in the cavity, such that the folding plunger when moved in axial direction hits the trailing haptic of the IOL, wherein the pushing plunger and the folding plunger are releasably connected by connecting means so that the pushing plunger and the folding plunger stay connected along a first displacement distance, and that the folding plunger is released from the pushing plunger along a second displacement distance, so that the pushing plunger only acts onto the IOL along the second displacement distance.

The objective is further in particular solved by a method for folding an IOL consisting of a optic part, a leading haptic and a trailing haptic in an IOL injector extending in an axial direction and comprising a distal end, a proximal end, a cavity, a pushing plunger and a folding plunge, the method comprising the steps of: inserting the IOL into the cavity such that the trailing haptic pointing to the proximal end and the leading haptic pointing to the distal end, further inserting the IOL such into the cavity that the pushing plunger, when moved in axial direction into the cavity, hits the optic part, further inserting the trailing haptic of the IOL such in the cavity that the folding plunger, when moved in axial direction into the cavity, hits the trailing haptic, moving the folding plunger and the pushing plunger together into the cavity so that the folding plunger hits the trailing haptic and folds the trailing haptic such that the trailing haptic is pointing to the distal end, releasing the pushing plunger and the folding plunger, and moving the pushing plunger so that it hits the optic part of the IOL and pushes the IOL with the trailing haptic pointing in distal direction to the distal end.

The objectives is further in particular solved by IOL injector system comprising: an IOL injector, a container containing an IOL and a lens holder for holding an IOL and further comprising a mechanism for releasing the IOL, the IOL injector and the container comprising connecting means adapted to connect and align the container with respect to the IOL injector such that the IOL can be transferred to within the cavity in a predetermined orientation.

One advantage of the invention is that the trailing haptic of an IOL is folded in a clearly defined, reproducible method step, thus avoiding high stress during folding and thus avoiding deforming the trailing haptic. In a preferred method and embodiment, the leading haptic is also folded in a clearly defined, reproducible method step, thus also avoiding high stress during folding. The folding is achieved without any direct manipulation of the IOL by a surgeon, as this was known in the state of the art, where the IOL had to be folded using a forceps. In addition the IOL has to be inserted into the IOL injector in a clearly defined orientation, thus leaving no space for erroneous placing the IOL in the injector. After folding, the IOL is pushed through a cavity and an injection nozzle in a clearly defined orientation, without any direct intervention, so that the whole IOL, after the haptics having been folded, is compacted in a clearly defined, reproducible step, thus avoiding high stress during compacting within the cartridge.

In a preferred embodiment, the IOL injector comprises only one pushing plunger that has to be pushed, for example at the thumb plate, even though the IOL injector comprises two plungers, a pushing plunger and a folding plunger that move within the injector body. Because in a preferred embodiment the folding plunger to a certain extent is connected with the pushing plunger, it is sufficient for a surgeon to activate only the pushing plunger for folding the IOL and pushing the IOL through the cartridge 5 and the injection nozzle 5a. One advantage of the IOL injector according to the invention therefore is that a surgeon is very familiar with handling such an injector, having only one single plunger to push. In addition the IOL injector according to the invention can consist of an injector body (a hand piece) and a separate cartridge, whereby the injector body is reusable or disposable and the separate cartridge is disposable. The IOL injector according to the invention can also be configured as a preloaded injector. The handling of both systems is very similar, so that a surgeon may use both systems, a preloaded system or a loadable system, without additional training. This also increases flexibility and safety, and decreases the cost for stocking and handling the injector system.

Various objects, features, aspects and advantages of the present invention will become more apparent from the following detailed description of preferred embodiments of the invention, along with the accompanying drawings in which like numerals represent like components.

DESCRIPTION OF PREFERRED EMBODIMENTS

Figure 1:
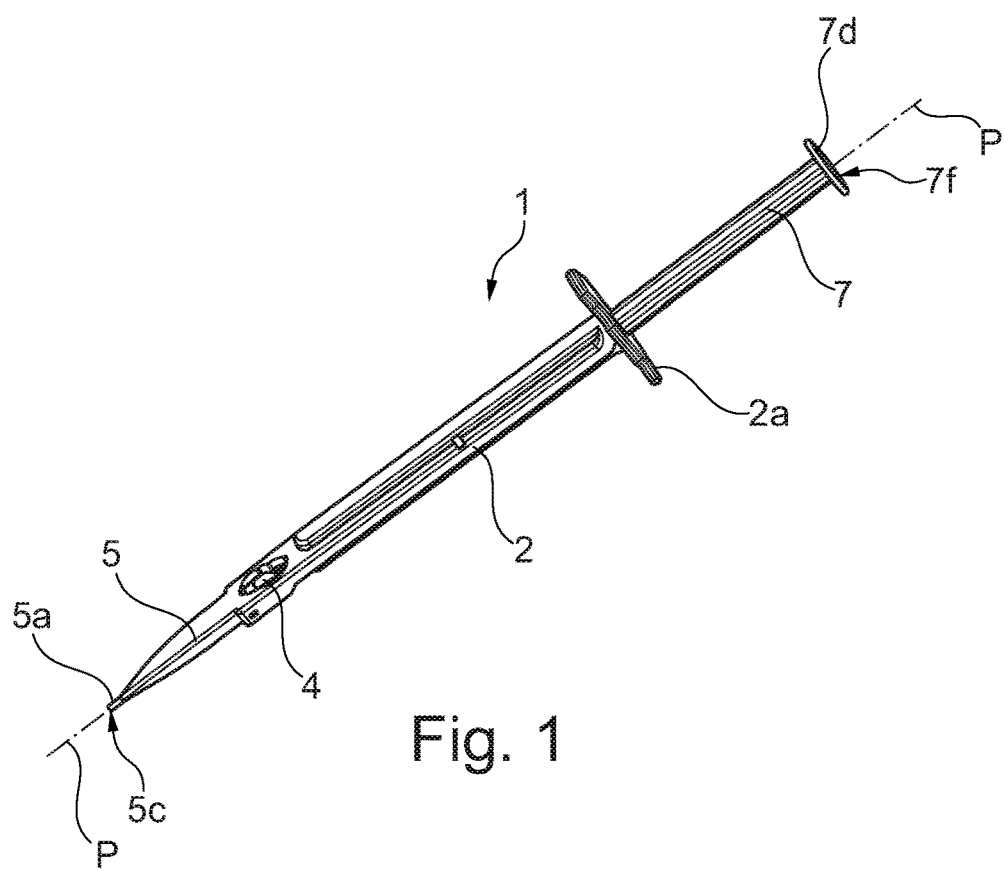
FIG. 1 is a perspective view of an IOL injector.

A preferred embodiment of the IOL injector 1 according to the present invention is shown in different views and cross sections in FIGS. 1 to 16. The IOL injector 1 shown in FIG. 1 includes an injector body 2 having a channel 6 extending in direction of the longitudinal axis P, along with a pushing plunger 7 slidably inserted in the injector body 2. The injector 1 further includes a cavity 4 for inserting an intraocular lens 100, and further includes a cartridge 5 with an injection nozzle 5a that ends at a distal end 5c. The injector body 2 having two finger grips 2a. The pushing plunger 7 at the opposite end of the distal end 5c having a thumb plate 7d, which also forms the proximal end 7f of the plunger 7, respectively the IOL injector 1. The channel 6 is extending through the injector body 2, the cavity 4 as well as the cartridge 5 and exits at the distal end 5c of the injection nozzle 5a, so that the pushing plunger 7 may advance an intraocular lens 100 positioned in the cavity 4. The term "pushing plunger" describes any component advanced through the channel 6 to push an intraocular lens 100 through the cavity 4 and the cartridge 5, so that the intraocular lens 100 exits the IOL injector 1 at the distal end 4 of the injection nozzle 5a. In a particular embodiment the injector body 2 may be a reusable hand piece, whereas the cartridge 5, which is releasably connected with the injector body 2, may be a single use part. In a further advantageous embodiment the injector body 2, the cartridge 5 and the cavity 4 may be formed as a single piece from a suitable material, which may include, for example polypropylene or polyethylene. The cartridge 5 may also be treated with a lubricious coating, a viscoelastic material and/or liquid in order to facilitate advancement of the IOL within the channel of the cartridge 5.

Figure 4:
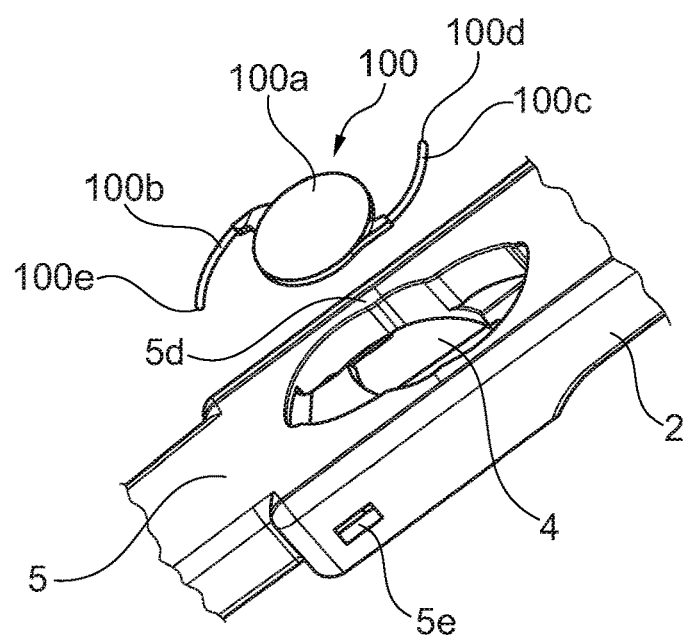
FIG. 4 is a perspective view of the loading cavity and an IOL.

The IOL 100 may be any intraocular lens formed of a flexible material, including but not limited to hydrogels, silicone or acrylic materials. The IOL 100 includes as least one optic part 100a and haptics 100b, 100c that stably fixate the IOL 100 within the eye when implanted. Each haptic 100b, 100c having one end anchored in the lens body 100a and a free end 100d, 100e for attachment to the eye tissue. The optic part 100a is structured to focus light onto a patient's retina, including the use of any suitable refractive and/or diffractive elements. FIG. 4 shows an IOL 100 positioned above the cavity 4 and ready to be inserted into the cavity 4. The IOL 100 disclosed is a three piece IOL with haptics 100b, 100c made of harder material than the optic part 100a. The two haptics 100b, 100c are herein called leading haptic 100b and trailing haptic 100c, depending on their position with respect to the distal end 5c and the proximal end 7f of the IOL injector 1, the leading haptic 100b extending in direction to the distal end 5c and the trailing haptic 100c extending in direction to the proximal end 7f, respectively the leading haptic 100b being positioned in direction to the distal end 5c of the cavity 4 and the trailing haptic 100c being positioned in direction to the proximal end 7f of the cavity.

Figure 2:
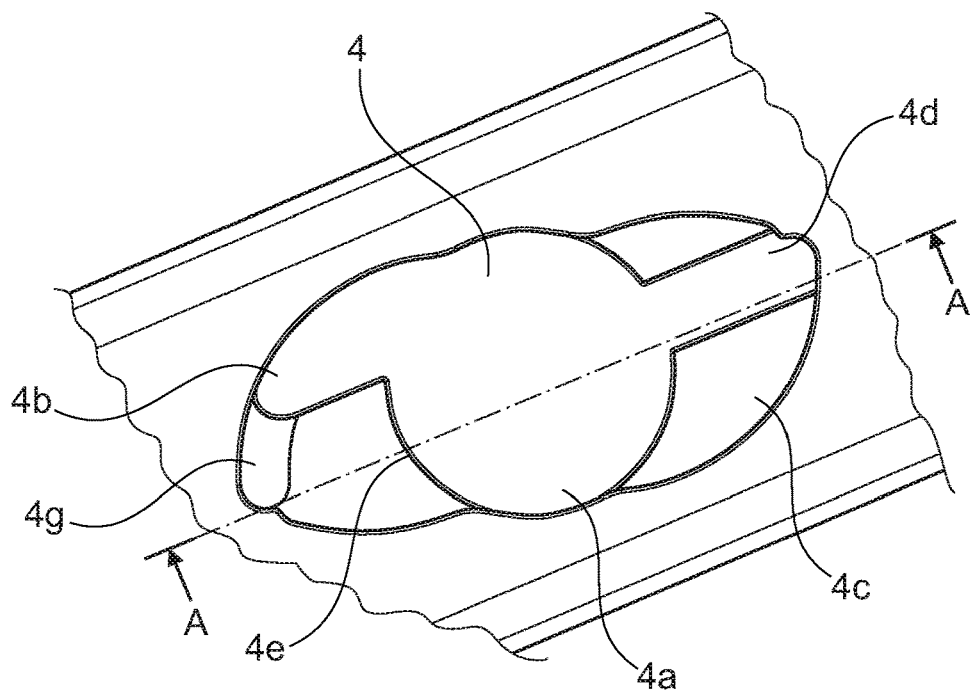
FIG. 2 is a top view of the loading cavity of the IOL injector.
Figure 3:
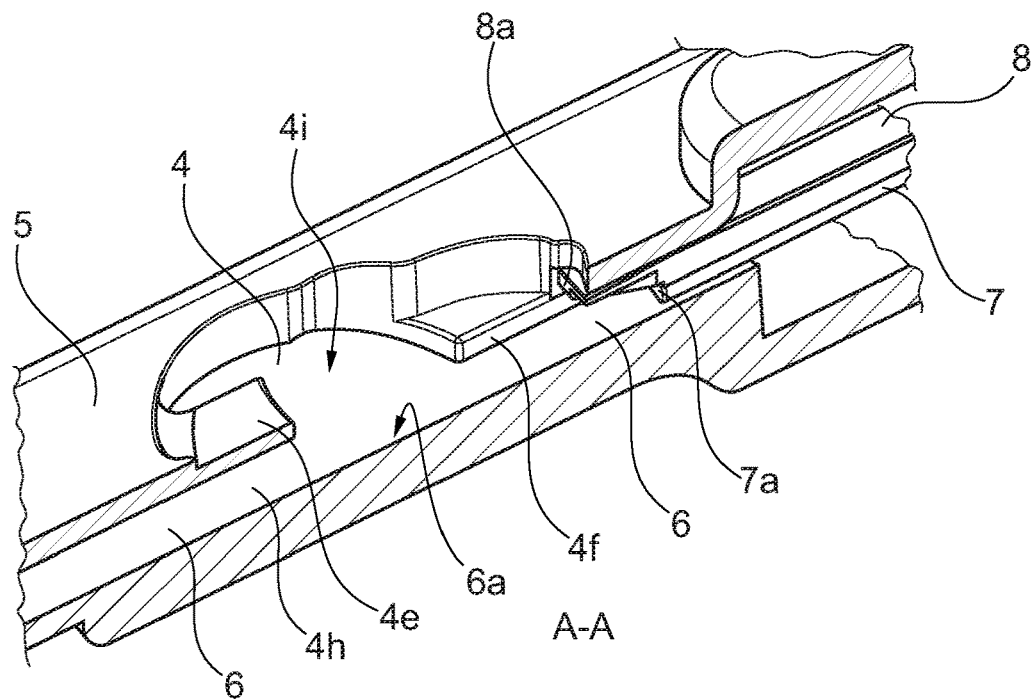
FIG. 3 is a sectional view along A-A of FIG. 2.

FIG. 2 shows a top view of the loading cavity 4. The loading cavity 4 serves to hold the IOL 100, in particular the optic part 100a as well as the leading haptic 100b and the trailing haptic 100c in a well-defined position. The loading cavity 4 includes a bottom 4a, a leading haptic nest 4b comprising a leading haptic rest 4g, a trailing haptic nest 4c. The loading cavity 4 further includes a longitudinal recess 4d, which is part of channel 6, and further includes a folding member 4e. FIG. 3 shows a sectional view of FIG. 2 along A-A. The channel 6 extends in direction of the longitudinal axis P and passes the cavity 4, so that the floor 6a of the channel 6 becomes the floor 4i of the cavity 4. The IOL injector 1 includes a pushing plunger 7 having a tip 7a, and includes a folding plunger 8 having a tip 8a, whereby the pushing plunger 7 is moveable along the bottom of channel 6, whereas the folding plunger 8 is arranged on top of pushing plunger 7. Both plungers 7, 8 are moveable in direction of the longitudinal axis P, so that they can pass the loading cavity 4, and through exit channel 4h can enter channel 6 of the cartridge 5. The folding member 4e is spaced apart from the floor 6a so that the two plungers 7, 8 may pass beneath the folding member 4e and enter the exit channel 4h.

FIG. 4 shows an IOL 100 correctly arranged above the loading cavity 4, and ready to be inserted into the loading cavity 4. FIG. 4 also shows an IOL injector 1 where the injector body 2 and the cartridge 5 are separate parts, both parts forming a part of the loading cavity 4, the cartridge 5 having a proximal end 5d, and the cartridge 5 being releasable connected with the injector body 2 by click 5e.

Figure 5:
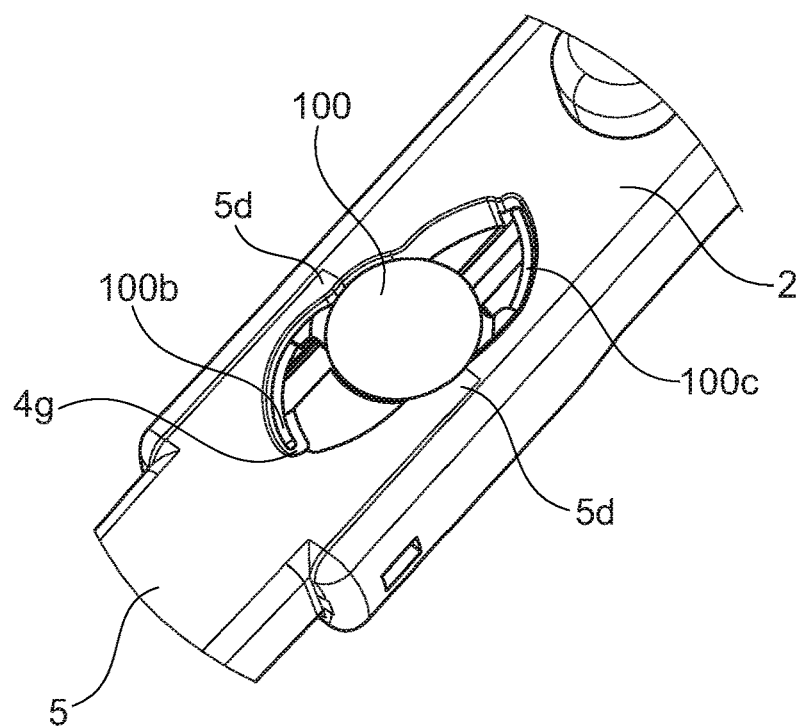
FIG. 5 is a perspective view of the loading cavity with the IOL partially inserted.
Figure 6:
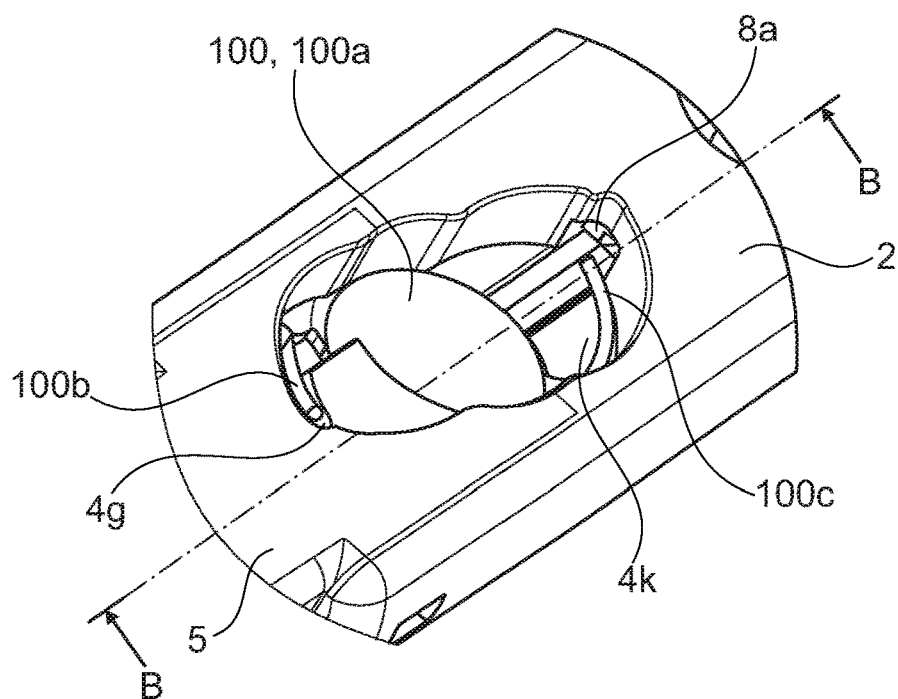
FIG. 6 is a perspective view of the loading cavity with the IOL fully inserted.
Figure 7:
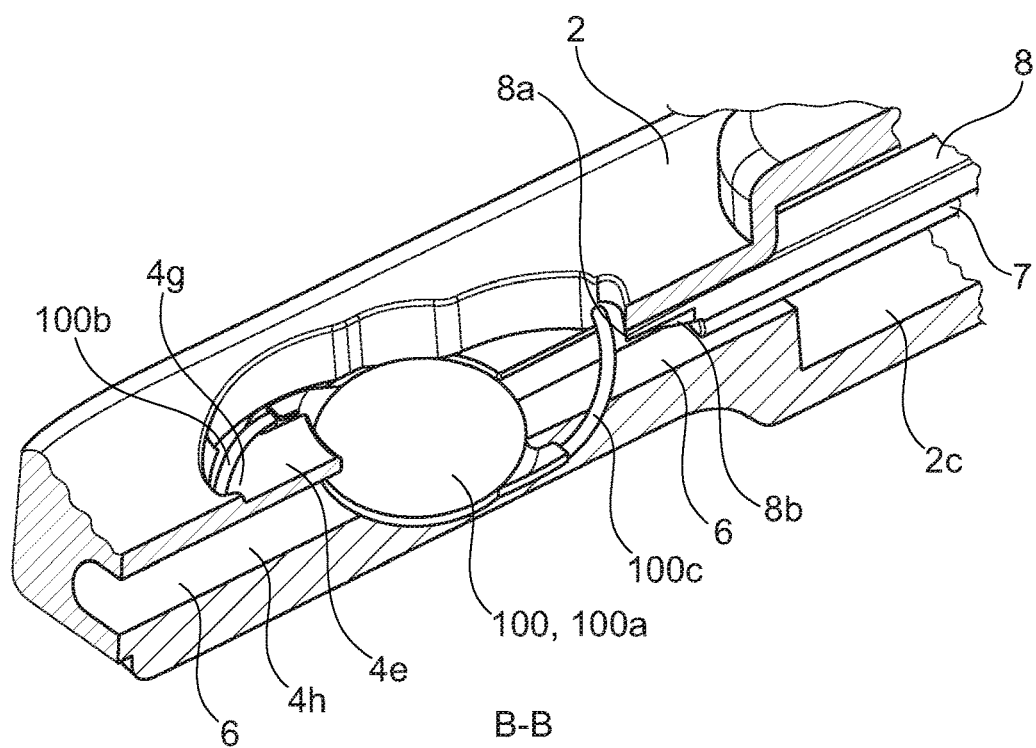
FIG. 7 is a sectional view along B-B of FIG. 6.
Figure 8:
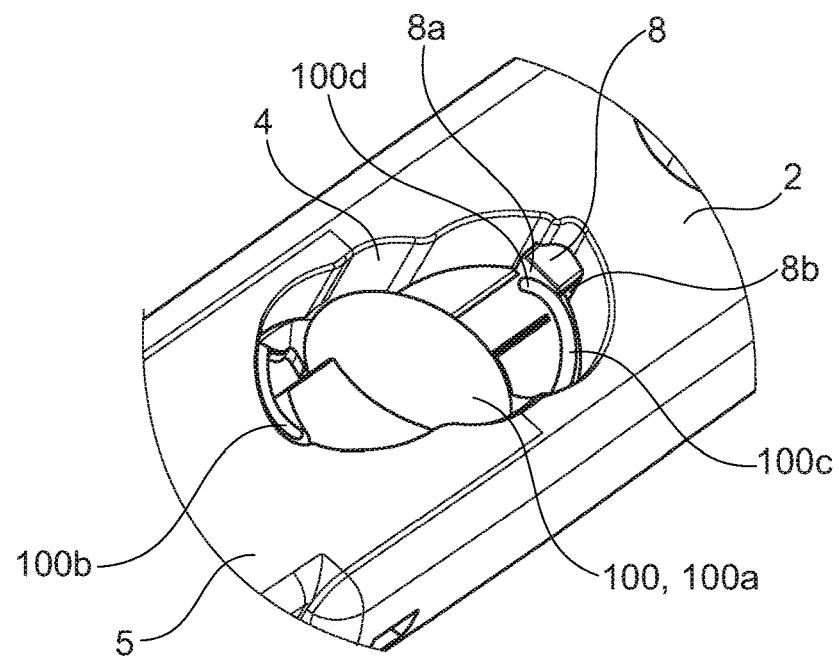
FIG. 8 is a perspective view of the cavity with fully inserted IOL and activated folding plunger.
Figure 9:
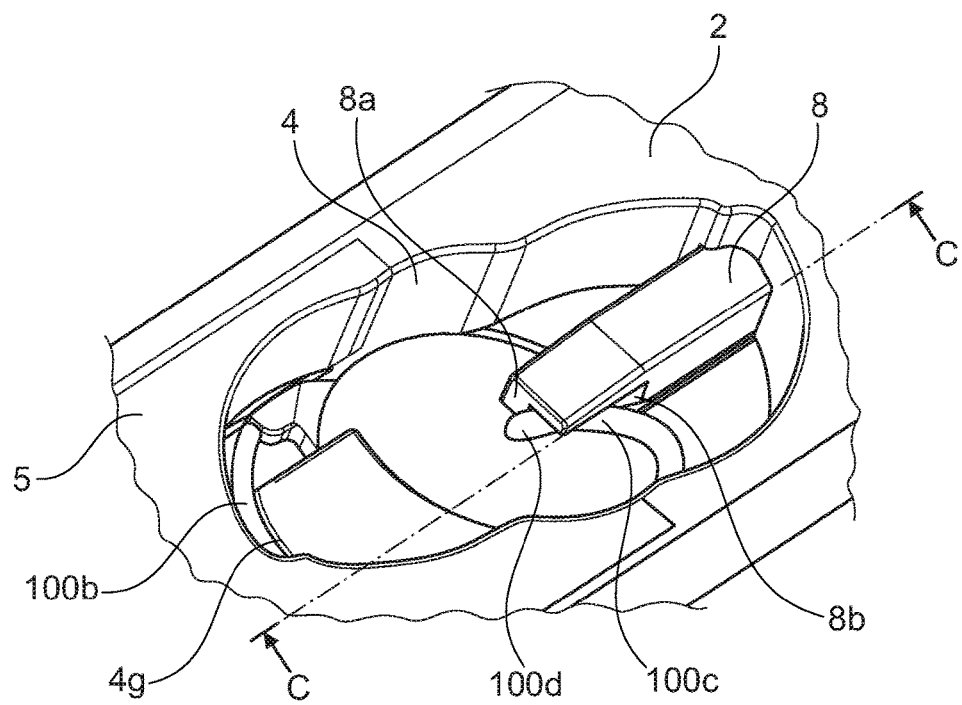
FIG. 9 is a perspective view of the loading cavity with activated folding plunger.
Figure 10:
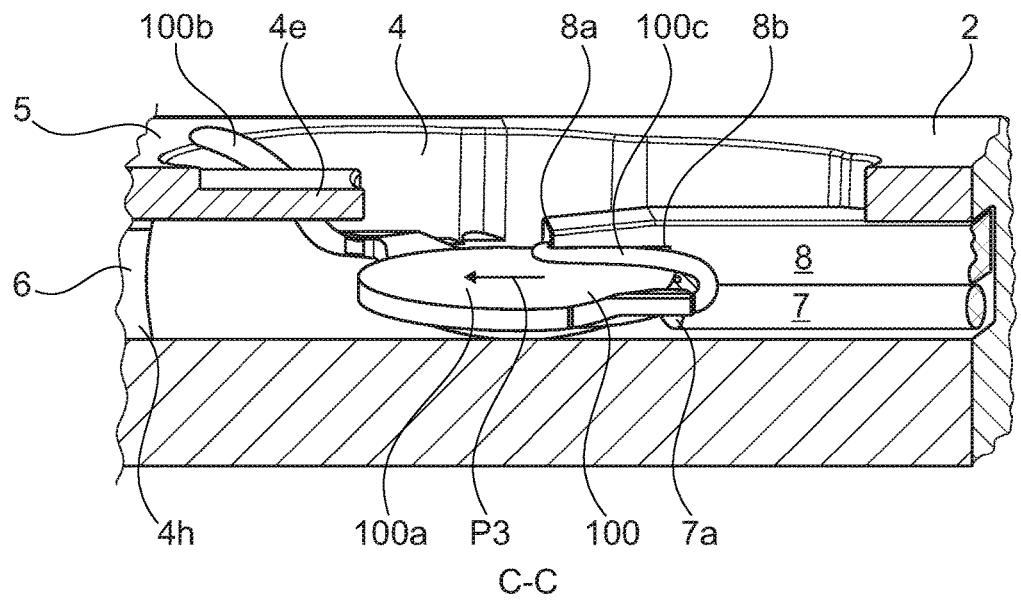
FIG. 10 is a sectional view along C-C of FIG. 9.
Figure 11:
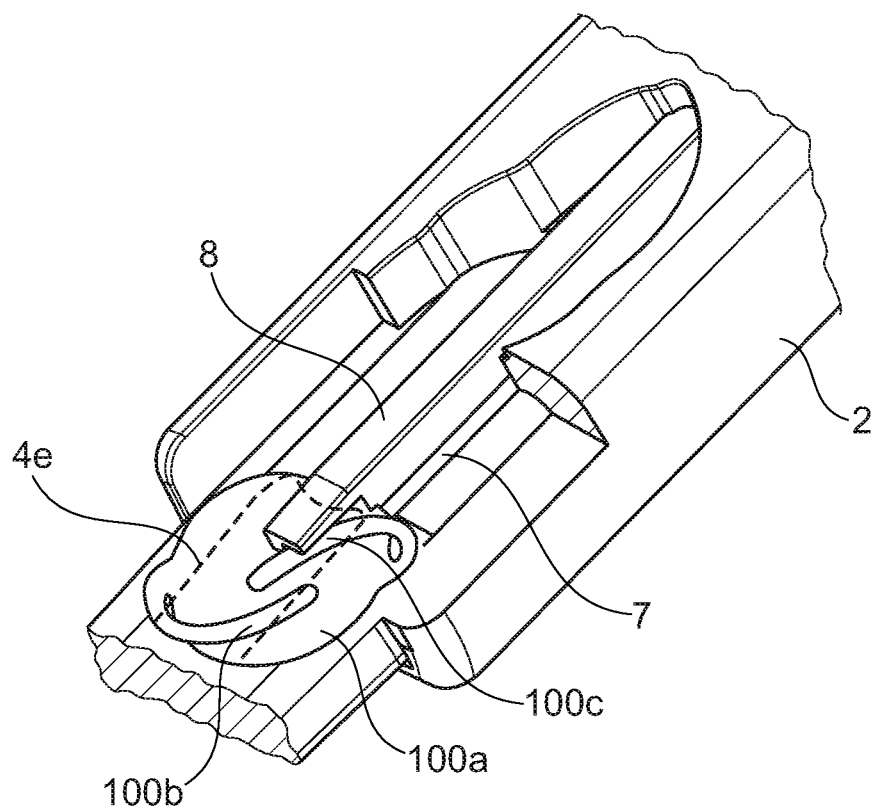
FIG. 11 is a perspective view of part of the loading cavity with activated folding plunger and pushing plunger.
Figure 12:
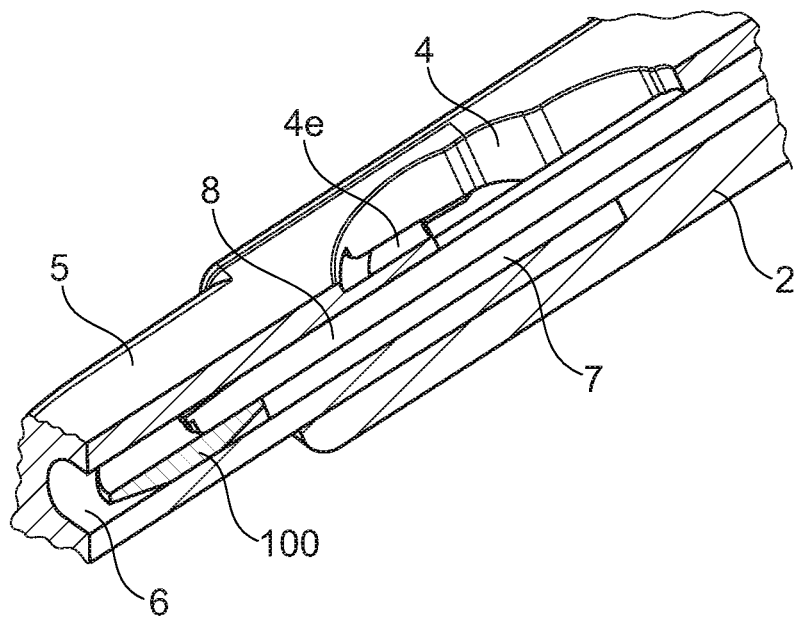
FIG. 12 is a longitudinal sectional view of the IOL injector, the IOL entering the tapered injection tube.

FIG. 5 shows the IOL 100 being partially inserted into the loading cavity 4, and FIG. 6 as well as FIG. 7 show the IOL 100 being fully inserted into the loading cavity 4, so that the optic part 100a rests on the floor 4i, the leading haptic 100b rests on the leading haptic rest 4g, and the trailing haptic 100c rests on the trailing haptic rest 4k, so that the position of the IOL 100, including lend 100, leading haptic 100b as well as trailing haptic 100c is well-defined with respect to channel 6, the pushing plunger 7 and the folding plunger 8. As can be seen in FIGS. 4, 5, and 6 pressing the IOL 100 all the way down into its end position in the cavity 4 has the effect that the haptics 100b, 100c bend upwards, out of the floor 4i of the channel 6 and the trailing haptic 100c becomes accessible for the folding plunger 8. Preferably the IOL 100 is elastically hold in the cavity 4 in its end position without additional holding means, but optionally holding means may be advantageous to actively hold down the IOL 100. As can best be seen in FIG. 7, the trailing haptic 100c is arranged such with respect to the folding plunger 8 that the folding plunger 8, when moved in axial direction P, hits with its tip 8a the trailing haptic 100c. In FIG. 8 the folding plunger 8 is slightly moving in direction of the cavity 4 and first hits the free end 100d of the trailing haptic 100c, and then folds the trailing haptic 100c in axial direction P, as disclosed in FIG. 9, so that the free end 100d of the trailing haptic 100c is pointing to the distal end 5c. Such an embodiment allows to carefully folding the trailing haptic 100c in axial direction, without excerting high pressure onto the haptic 100c, so that a deformation of the trailing haptic 100c due to folding can be avoided. In a preferred embodiment the folding plunger 8 also comprises a guiding and holding element 8b such as a bevel 8b at the tip 8a, which guides the trailing haptic 100c and makes sure that the trailing haptic 100c keeps its position after folding. FIG. 10 is a sectional view of FIG. 9 along C-C. The folding plunger 8 and the pushing plunger 7 are moving together in direction of the longitudinal axis P. FIGS. 9 and 10 show the moment, when the pushing plunger 7 hits the optic part 100a of IOL 100. As the folding plunger 8 and the pushing plunger 7 continue to move in moving direction P3, the IOL 100 is moved in moving direction P3, and moves underneath the folding member 4e to exit 4h, where the IOL 100 enters channel 6 of the cartridge 5. At least part of the haptic rest 4g extends along the folding member 4e, on the upper side of folding member 4e, so that, when the IOL 100 is moved in moving direction P3, the leading haptic 100b is flipped with respect to the optic part 100a, as shown in FIG. 11. In FIG. 11, part of the cartridge 5 is not shown, and the position off the folding member 4e is just indicated, to get a clear view of the position of the leading haptic 100b and the trailing haptic 100c of the IOL 100. The IOL 100 in this configuration is pushed into channel 6 of the cartridge 5. In the embodiment disclosed the pushing plunger 7 and the folding plunger 8 together move in direction P3. FIG. 12 shows the IOL 100 within channel 6 of the cartridge 5. The IOL 100 is only schematically shown, in particular no details of the haptics 100b, 100c are shown.

Figure 13:
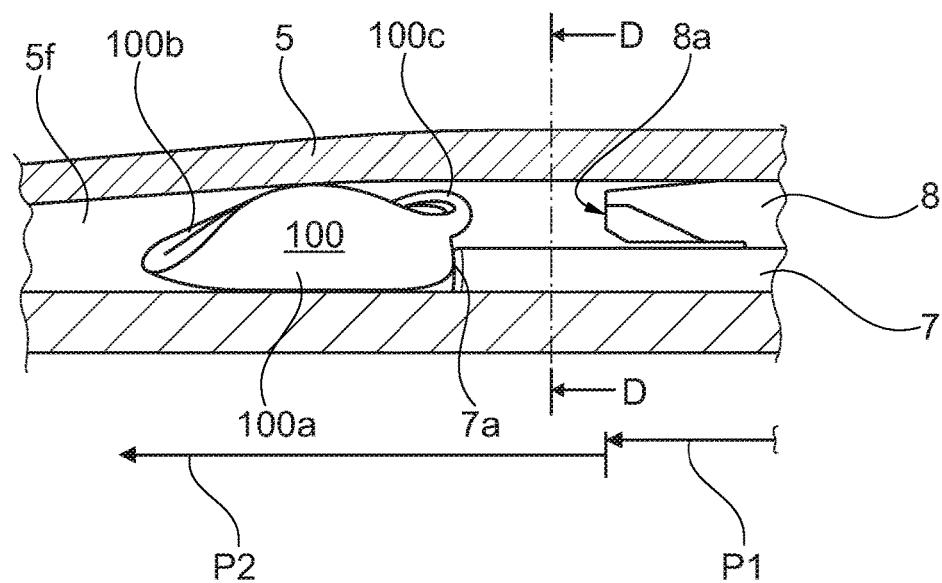
FIG. 13 is a further longitudinal sectional view of the IOL within the tapered injection tube.
Figure 14:
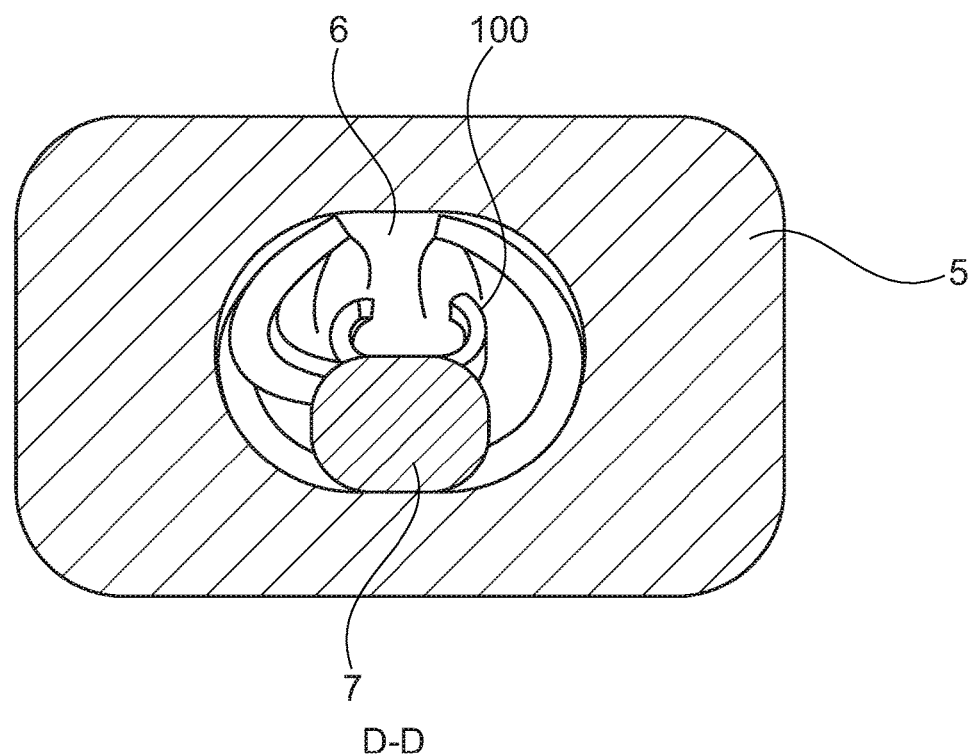
FIG. 14 is a sectional view along D-D of FIG. 13.

FIG. 13 shows a longitudinal sectional view of the cartridge 5 and FIG. 14 a sectional view along D-D of FIG. 13. After starting to push the plungers 7, 8 in FIG. 6, the movement of the folding plunger 8 is stopped at the end of a first displacement distance P1, and the pushing plunger 7 continues moving in channel 6, so that the IOL 100 enters the tapered end section 5f and then leaves channel 6 at the injection nozzle 5a. The movement of pushing plunger 7 is stopped at the end of the second push distance P2. FIG. 14 schematically shows the IOL 100 within channel 6, with haptics 100b, 100c folded in axial direction, and being compacted and pushed by the pushing plunger 7 in distal direction and afterwards through the injection nozzle 5a.

In a further embodiment no folding member 4e is arranged in the cavity 4, and preferably also no leading haptic rest is arranged, so that the leading haptic 110b of an IOL 100 inserted into the cavity 4 comes to rest on the floor 4i of the channel 6. When the IOL 100 is pushed in direction P3, as disclosed in FIG. 10, the leading haptic 100b will be pushed into channel 6, so that within channel 6 of the cartridge 5, the free end 100e of the leading haptic 100b is directed in distal direction and the free end 100d of the trailing haptic 100c is also direction in distal direction. The IOL 100 may in this configuration be pushed through channel 5 and the injection nozzle 5a.

Figure 15:
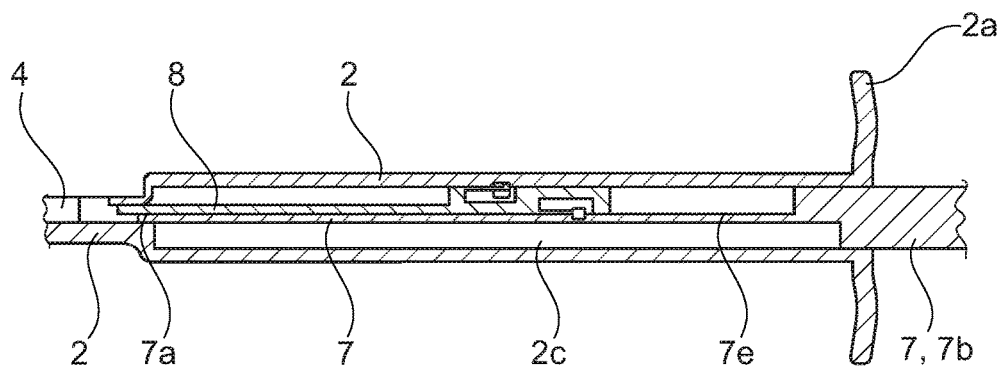
FIG. 15 is a longitudinal sectional view of the IOL injector.
Figure 16:
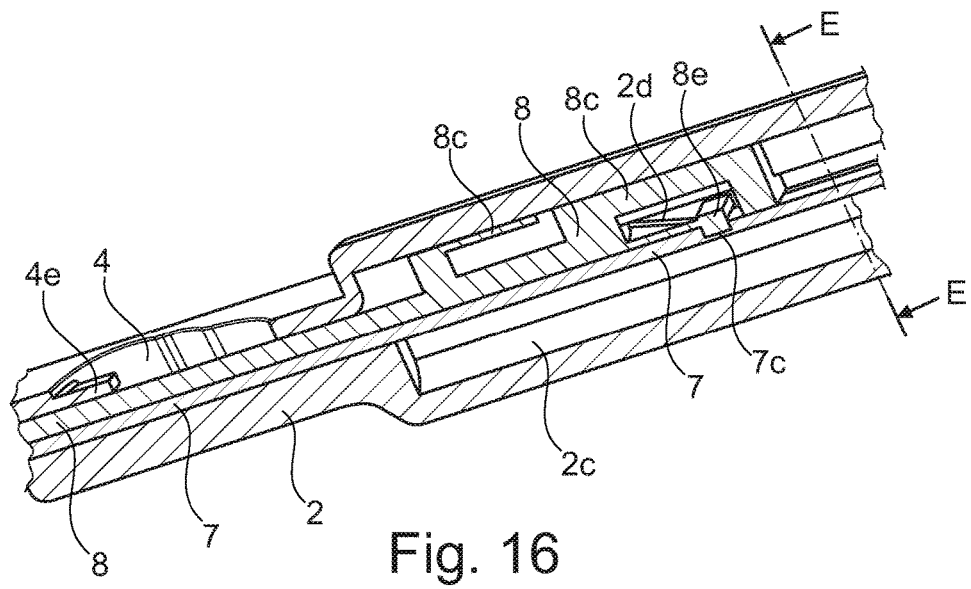
FIG. 16 is a further longitudinal sectional view of the IOL injector.
Figure 16A:
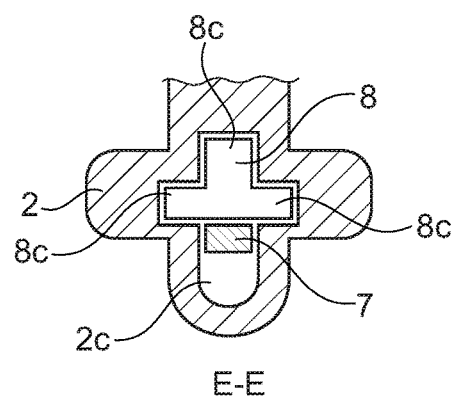
FIG. 16a is a section view along E-E of FIG. 16.

FIGS. 15 and 16 show longitudinal sectional views of a preferred embodiment of the injector body 2, the pushing plunger 7 and the folding plunger 8. The pushing plunger 7 extends from the proximal end part 7b, ending at the proximal end 7f, up to the tip 7a. The folding plunger 8 is a separate plunger arranged within channel 6 and moveable in direction of the longitudinal axis P. As disclosed in FIG. 16, the folding plunger 8 comprises guiding elements 8c which contact the outer wall of the injector body 2, so that the folding plunger 8 is guided between the outer wall and the pushing plunger 7. FIG. 16a shows a sectional view along E-E of FIG. 16. The folding plunger 8 comprises three guiding elements 8c. Below the pushing plunger 7 an optional spring chamber 2c is arranged. The pushing plunger 7 and the folding plunger 8 are releasably connected by connecting means 7c, 8e. The folding plunger 8 comprises a locking element 8e and the pushing plunger comprises a recess 7c, so that the folding plunger 8 is connected with the pushing plunger 7, so that they move together in direction of the longitudinal axis P, up to the end of the first displacement distance P1. The inner wall of the injector body 2 comprises a groove or ramp 2d which lifts the locking element 8e when the folding plunger 8 is slidably advancing in direction of the distal end 5c and reaches the end of the first displacement distance P1, so that the folding plunger 8 is not connected any more with the pushing plunger 7. The movement of the folding plunger 8 is therefore stopped, whereas the pushing plunger 7 continues to move as long as the surgeon applies a pressure onto the thumb plate 7d. There are various options to build connecting means 7c, 8e, such as mechanical connecting means, or motor driven connecting means. In a preferred embodiment, a spring is inserted in the chamber 2c, for example in the embodiment disclosed in FIG. 15. A spring extending within the chamber 2c and acting on the distal side onto the injector body 2 and on the proximal side onto the proximal end part 7b of the pushing plunger 7 has the effect, that the pushing plunger 7 returns back to the position disclosed in FIG. 15, as soon as no pressure is applied onto the thumb plate 7d. In addition the spring gives a tactile feedback to the surgeon when pushing the thumb plate 7d. Alternative embodiments could use any other suitable technique for advancing, and if necessary returning the plungers 7,8 including, for example, a knob that is turned to advance a plunger in threaded engagement with the channel 6, or even a motorized injector that is triggered electronically. In a preferred embodiment the IOL injector 1 may comprise one motor drive, driving the pushing plunger 7, whereby the folding plunger 8 is activated as described in FIGS. 1 to 16. In a further embodiment the IOL injector 1 may comprise two motor drives, one drive for each plunger 7, 8, so that the two plungers 7, 8 may be activated independently. In such an embodiment, it is not necessary that the folding plunger 8 protrudes the pushing plunger 7 in distal direction before the IOL injector 1 is activated. After activation of the IOL injector, the drive driving the folding plunger 8 could first be activated and afterward the drive driving the pushing plunger 7 could be activated, so that the folding plunger 8 protrudes the pushing plunger 7 when entering the cavity 4. The motor drives could be an electrical drive, but for example also a pneumatic drive or a hydraulic drive.

Figure 17:
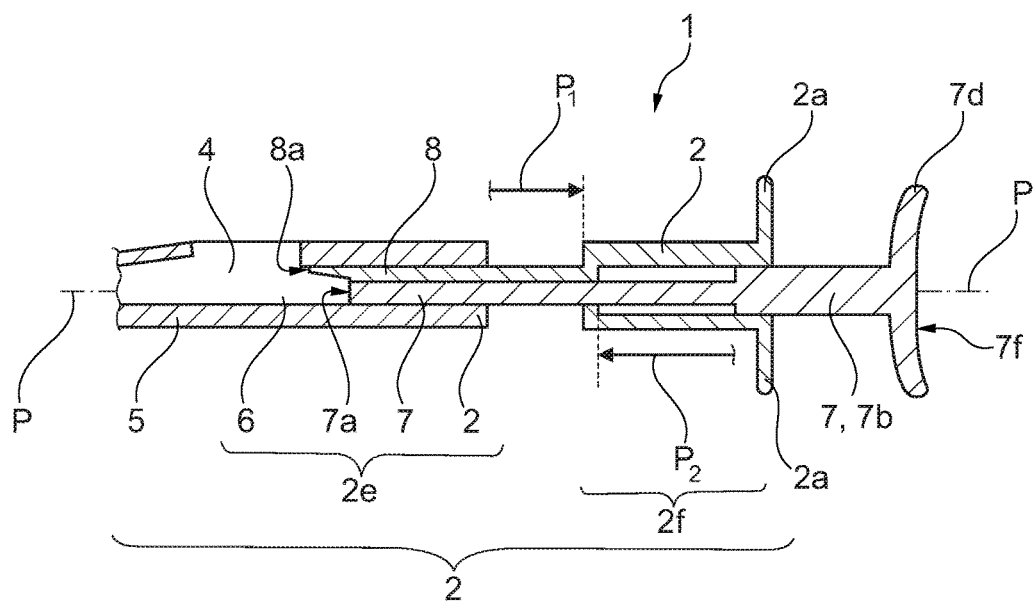
FIG. 17 is a schematic longitudinal sectional view of a further embodiment of an IOL injector.

FIG. 17 shows schematically a longitudinal sectional view of a further embodiment of an IOL injector 1. The cavity 4 is only schematically shown and can be configured as disclosed in one of FIGS. 2 to 10. The injector body 2 is split in two parts and comprises a front section 2e and a gripping section 2f. The cavity 4, the cartridge 5 and the channel 6 leading to the cavity 4 may be built as disclosed in FIGS. 2 to 14. The pushing plunger 7 and the folding plunger 8 may be arranged in front of the cavity 4 as disclosed in FIG. 3 or 7, in that the tip 8a of the folding plunger 8 projects the tip 7a of the pushing plunger 7. Similar to the embodiments disclosed in FIGS. 15 and 16, the pushing plunger 7 consists of one piece and extends from the thumb plate 7d up to the tip 7a. In contrast to the embodiment disclosed in FIGS. 15 and 16, the folding plunger 8 disclosed in FIG. 17 is connected with the gripping section 2f of the injector body 2. The front section 2e and the gripping section 2f are spaced apart in a distance of the first displacement P1 in axial direction P. The pushing plunger 7 is moveable in the gripping sections along a distance of the second displacement P2. The IOL injector 1 disclosed in FIG. 17 is handled such that in a first step the IOL 100 is inserted into the cavity 4, as disclosed in FIGS. 4, 5, and 6. In a second step the front section 2e and the gripping section 2f are pushed together, along the distance of the first displacement P1, until the front section 2e and the gripping section 2f contact each other. During this second step, the haptics 100b, 100c are folded and the IOL 100 introduced into channel 6 of cartridge 5, as disclosed in FIGS. 7 to 12. In a third step the pushing plunger 7 is pushed along the distance of the second displacement P2, as disclosed in FIGS. 13 and 14, thereby pushing the IOL 100 out of the injection nozzle 5a. The IOL injector 1 also comprises connecting means 7c, 8e, which are not shown in detail, for releasably connecting the pushing plunger 7 and the folding plunger 8. Such connecting means 7c, 8e are shown in detail in FIG. 20.

Figure 18:
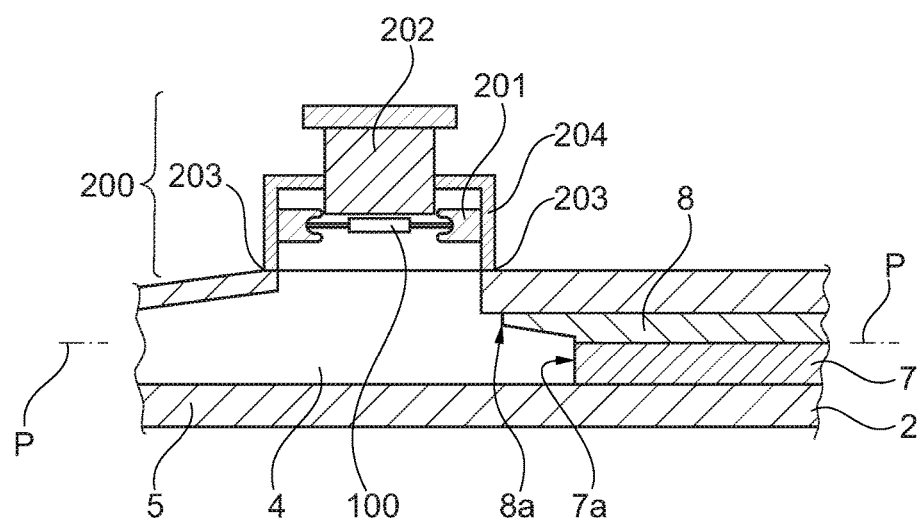
FIG. 18 is a longitudinal sectional view of an IOL injector system.

FIG. 18 schematically shows an embodiment of an IOL injector system comprising an IOL injector 1 and a container 200 containing an IOL 100. The container 200 comprises a casing 204 and a lens holder 201 to hold the IOL 100. The container 200 further comprises a mechanism 202 to release the IOL 100. In the embodiment disclosed, a releasing plunger 202 is acting onto the lens holder 201 to release the IOL 100 and to transfer the IOL 100 into the cavity 4 underneath, so that the IOL 100 comes to rest in the cavity 4 as disclosed in FIG. 6. In a preferred embodiment the container 200 containing the IOL 100 is a separate unit, and the container 200 and the IOL injector 1 comprising connection means 203, so that the container 200 may be correctly aligned with the IOL injector 1, attached to the IOL injector 1 and the IOL 100 may be transferred to within the cavity 4. In a further embodiment, the IOL injector 1 is a preloaded system such that the container 200 is part of the IOL injector 1, and the IOL 100 may be transferred to within the cavity 4 at the time the IOL injector 1 is used.

Figure 19:
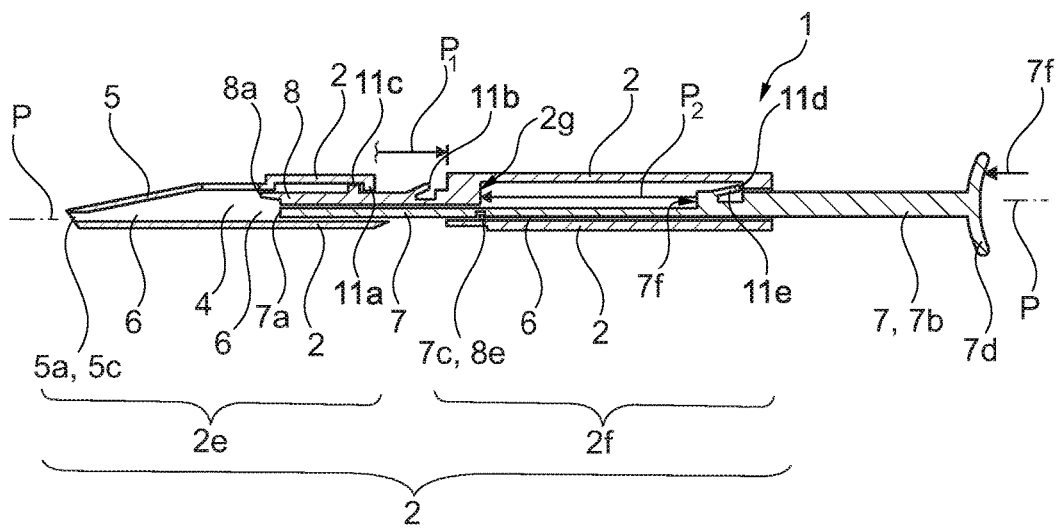
FIG. 19 is a longitudinal sectional view of a further embodiment of an IOL injector.
Figure 20:
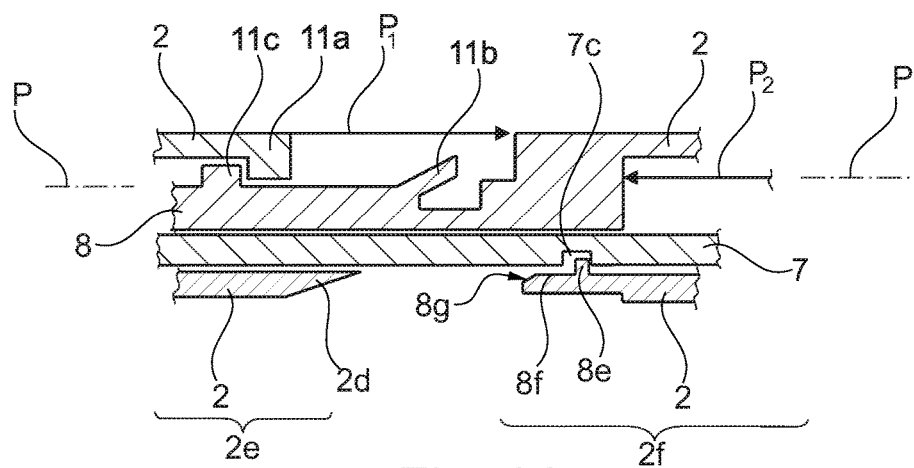
FIG. 20 is a detailed view of the IOL injector according to FIG. 19.

FIG. 19 shows a longitudinal sectional view of a further embodiment of an IOL injector 1 comprising an injector body 2 split into two parts, a front section 2e and a gripping section 2f. The embodiment disclosed in FIG. 19 is similar to the embodiment disclosed in FIG. 17, but shows more details, and in particular shows an embodiment of connecting means 7c and 8e. The connecting means 11b and 11c are part of the gripping section 2f. The connecting means 11a is part of the front section 2e. The connecting means 11a, 11c are arranged to define the maximal length of first displacement distance P1. The front section 2e cannot be moved further in axial direction P than the first displacement distance P1. The purpose of the connecting means 11b is to keep the connecting means 11a and thereby the front section 2e in a defined position with respect to the injector body 2 as soon as the front section 2e has been moved along the first displacement distance P1, so that the connecting means 11b snappably connects with the connecting means 11a, so that no relative movement between the front section 2e and the gripping section 2f is possible any more in axial direction P, so that the injector body 2 stays connected. The injector body 2 comprises a front side 2g and the pushing plunger 7 comprises a front side 7f, whereby the two front sides 2g, 7f are arrange opposite each other and the distance there between defining the second displacement distance P2. The injector body 2 further comprising a recess 11d and the pushing plunger 7 comprising a locking element 11e which acts onto the recess 11d in such a way that, in the position disclosed in FIG. 19, the injector body 2 and the pushing plunger 7 can't move independently to the right, but the pushing plunger 7 can be moved independently from the injector body 2 to the left as long as the front sides 2g, 7f do not touch each other. FIG. 20 shows the connections means 7c, 8e disclosed in FIG. 19 in more details. The injector body 2 of the gripping section 2f comprises a spring element 8f having a locking element 8e and a ramp 8g. The pushing plunger 7 comprises a recess 7c, whereby the locking element 8e and the recess 7c, as disclosed in FIG. 20, are arranged such that the pushing plunger 7 and the injector body 2 of the gripping section 2f are connected and therefore can't move independently into axial direction P. The injector body 2 of the front section 2e comprises a guiding means 2d, a ramp, projecting into the direction of the ramp 8g. Then the front section 2e is moved versus the gripping section 2f, along the first displacement distance P1, the guiding means 2d acts onto the ramp 8g and thereby lifts the spring element 8f, so that the locking element 8e leaves the recess 7c, so that the pushing plunger 7 can be moved relative to the injector body 2, along the second displacement distance P2. FIGS. 19 and 20 therefore show that the pushing plunger 7 and the folding plunger 8 are releasably connected by connecting means 7c, 8e, so that the pushing plunger 7 and the folding plunger 8 stay connected along the first displacement distance P1, and the folding plunger 8 is released from the pushing plunger 7 along the second displacement distance P2, so that the pushing plunger 7 may be moved independently from the folding plunger 8.

In the most preferred embodiment the IOL injector 1 disclosed in FIGS. 19 and 20 is operated as follows: In a first step the IOL 100 is introduced into the cavity 4. In a second step the cartridge 5 is pushed along the first displacement distance P1 until the connecting means 11b and 11a connect with each other so that the cartridge 5 contacts the injector body 2, so that the front section 2e and the gripping section 2f are connected, forming the injector body 2. In this position, with is not shown in FIG. 19, the IOL 100 rests folded within the cartridge 5. The IOL 100 is now ready to be inserted into the eye. A force 7f is applied onto the thumb plate 7d so that the plunger 7 is moved along the second displacement distance P2, and the IOL 100 is pushed by the front side 7a of the plunger 7 through the distal end 5c of the cartridge 5 into the eye. FIGS. 19 and 20 show the movement of the first displacement distance P1 and the second displacement distance P2 in opposite direction. The IOL injector 1 may also be operated such that the first displacement distance P1 and the second displacement distance P2 move in the same axial direction P.

Figure 21:
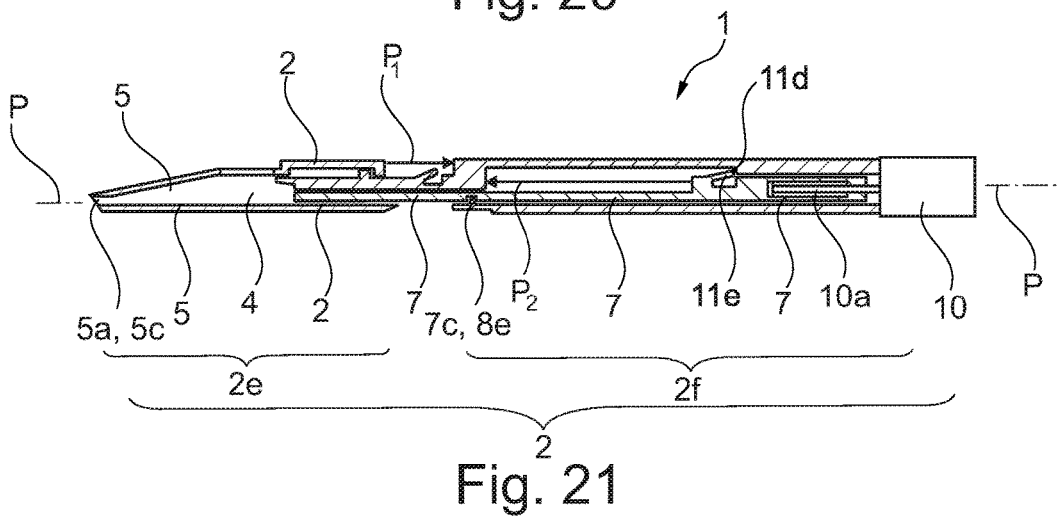
FIG. 21 is a longitudinal sectional view of a further embodiment of an IOL injector.

FIG. 21 shows a longitudinal sectional view of a further embodiment of an IOL injector 1. The IOL injector 1 disclosed in FIG. 21 distinguishes in so far from the embodiment disclosed in FIG. 19, as a motor drive 10 is used instead of the thumb plate 7d, to move the plunger 7 along the second displacement distance P2. The motor drive 10 comprises a motor shaft 10a that acts onto the plunger 7 to push the plunger 7 along the second displacement distance P2.

The embodiment disclosed in FIGS. 1 to 15 could easily be modified to also be motor driven. The motor 10 disclosed in FIG. 21 could easily be arrange to connect the injector body 2 and the plunger 7, as can be seen in FIG. 15, so that the pushing plunger 7 needs no thumb plate 7d, and the motor 10 acting onto the pushing plunger 7 drives the plunger 7 to the left in axial direction P in direction of the distal end 5c. Because the folding plunger 8 is coupled to the pushing plunger 7, also the folding plunger 8 is driven by motor 10. Therefore, in an advantageous embodiment, the IOL injector 1 according to the invention can be motor driven, which allows a very convenient handling of the IOL injector 1.

In a preferred embodiment, after opening the packaging of the container 200, the lens may be half way down in the loading cavity 4 of the IOL injector 1, which means further down than disclosed in FIG. 18. The IOL 100 is still fixed in place by the holding mechanism 201. Pressing the IOL 100 or the releasing mechanism 202 down has the effect that the lens elastically leaves the holding mechanism 201 and moves down to the loading cavity 4, so that the IOL injector 1 is ready for use, which means ready for activating the plunger 7. Optionally the holding mechanism 201 or parts thereof may serve as the pusher 202.

A preferred method for folding the IOL 100 consisting of a optic part 100*a*, a leading haptic 100*b* and a trailing haptic 110*c* in an IOL injector 1 extending in an axial direction P and comprising a distal end 5*c*, a proximal end 7*f*, a cavity 4, a pushing plunger 7 and a folding plunge 8, comprising the steps of:

inserting the IOL 100 into the cavity 4 such that the trailing haptic 110*c* pointing to the proximal end 7*f* and the leading haptic 100*b* pointing to the distal end 5*c*, further inserting the IOL 100 such into the cavity 4 that the pushing plunger 7, when moved in axial direction P into the cavity 4, hits the optic part 100*a*, further inserting the trailing haptic 110*c* of the IOL 100 such in the cavity 4 that the folding plunger 8, when moved in axial direction P into the cavity 4, hits the trailing haptic 110*c*, moving the folding plunger 8 into the cavity 4 so that it hits the trailing haptic 100*c* and folds the trailing haptic 100*c* such that the trailing haptic 100*c* is pointing to the distal end 5*c*, and moving the pushing plunger 7 so that it hits the optic part 100*a* of the IOL 100 and pushes the IOL 100 with the trailing haptic 100*c* pointing in distal direction to the distal end 5*c*.

In a further preferred method step, the method also comprises the step of inserting the IOL 100 in the cavity 4 such that the leading haptic 100*b* being arranged in a leading haptic rest 4*g* and a folding member 4*e*, moving the pushing plunger 7 so that it hits the optic part 100*a* of the IOL 100 and pushes the IOL 100 in distal direction, so that the leading haptic 100*b* is folded by the folding member 4*e* such that the leading haptic 100*b* is pointing to the proximal end 7*f*, and moving the pushing plunger 7 so that it pushes the IOL 100 with the trailing haptic 100*c* pointing in distal direction and the leading haptic 100*b* pointing in proximal direction to the distal end 5*c*.

The injector body 2 holds the cartridge 5. The cartridge 5 can be releasably attached to the injector body 2. The cartridge 5 could be delivered separately. The injector body 2 including plungers 7, 8 could be a multiuse device, whereas the cartridge 5 could be a single use device. The injector body 2 and the cartridge 5 could also be manufactured as one single part.

While certain embodiments of the present invention have been described above, these descriptions are given for purposes of illustration and explanation. Variations, changes, modifications and departures from the devices and methods disclosed above may be adopted without departure from the scope of the present invention as claimed.

The invention claimed is:

1. IOL (intraocular lens) injector for introducing an IOL into the eye, comprising:
    an injector body;
    a cavity for holding the IOL comprising a leading haptic and a trailing haptic;
    a cartridge ending at a distal end in an injection nozzle;
    the injector body, the cavity and the cartridge having a channel extending in axial direction;
    an axially movable pushing plunger being placed in the channel of the injector body for pushing the IOL in axial direction out of the cavity and into the cartridge and the injection nozzle,
    and a folding plunger that is arranged in the channel and is extending in axial direction, parallel to the pushing plunger;
    wherein the cavity comprises a trailing haptic rest for defining the direction of the trailing haptic of an IOL arrange in the cavity, such that the folding plunger when moved in axial direction hits the trailing haptic of the IOL,
    that the pushing plunger and the folding plunger are releasably connected by connecting means, so that the pushing plunger and the folding plunger stay connected along a first displacement distance, and that the folding plunger is released from the pushing plunger along a second displacement distance, so that the pushing plunger only acts onto the IOL along the second displacement distance.

2. The IOL injector according to claim 1, wherein the folding plunger is arranged such in the injector body that the folding plunger protrudes beyond the pushing plunger in direction of the distal end, so that the folding plunger, when moved in axial direction, first contacts the trialing haptic of the IOL, such that the folding plunger folds the trailing haptic in direction of the distal end.

3. The IOL injector according to claim 1, wherein the cavity comprising a leading haptic nest directed in distal direction and a trailing haptic nest directed in proximal direction, opposite to the distal end.

4. The IOL injector according to claim 3, wherein the leading haptic nest comprises a leading haptic rest for defining the direction of the leading haptic of an IOL arranged in the cavity, and wherein the leading haptic nest comprises a folding member arranged on the distal side of the cavity, wherein the folding member is arranged above the channel, and wherein at least part of the leading haptic rest extends along the folding member.

5. The IOL injector according to claim 1, wherein the cavity has a bottom which extends along the floor of the channel.

6. The IOL injector according to claim 1, wherein the injector body comprises guiding means, wherein the guiding means and the connecting means are arranged such and interact such, that the connecting means open between the first and second displacement distance.

7. The IOL injector according to claim 1, comprising a motor that acts onto the pushing plunger to drive the pushing plunger in axial direction.

8. The IOL injector according to claim 1, wherein the injector body comprises a distal part and a proximal part, wherein the distal part and the proximal part are spaced apart along a first displacement distance in axial direction, wherein the distal part and the proximal part are moveable in axial direction along the first displacement distance, wherein the folding plunger is connected with the proximal part, and wherein the folding plunger is extending and axially moveable within a channel of the distal part, and wherein a proximal end part of the pushing plunger is moveable in axial direction along a second displacement distance in the proximal part and wherein the pushing plunger is extending from the proximal end part in distal direction and is extending in axial direction and axially moveable within the channel of the distal part, wherein, in a loading position of the IOL injector, a tip of the pushing plunger and a tip of the folding plunger are directed versus the cavity, wherein the folding plunger in particular is part of the proximal part of the injector body.

9. The IOL injector according to claim 1, wherein the injector body and the cartridge are separate components releasably connected to each other.

10. The IOL injector according to claim 1, wherein the injector body and the cartridge is a single component.

11. The IOL injector system comprising:
   an IOL injector according to claim 1,
   a container containing an IOL and a lens holder for holding the IOL and further comprising a mechanism for releasing the IOL;
   the IOL injector and the container comprising connecting means adapted to connect the container with respect to the IOL injector such that the IOL can be transferred to within the cavity.

12. The IOL injector system according to claim 11, wherein the container is connected and aligned such with respect to the IOL injector that the IOL may be transferred to within the cavity by linear movement.

\* \* \* \* \*